(12) United States Patent
Nakamura

(10) Patent No.: US 10,863,884 B2
(45) Date of Patent: Dec. 15, 2020

(54) FLEXIBLE TUBE INSERTION APPARATUS COMPRISING INSERTION SECTION TO BE INSERTED INTO SUBJECT AND METHOD OF OPERATING THEREOF

(71) Applicant: OLYMPUS CORPORATION, Tokyo (JP)

(72) Inventor: Shuji Nakamura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 15/866,534

(22) Filed: Jan. 10, 2018

(65) Prior Publication Data

US 2018/0184884 A1    Jul. 5, 2018

Related U.S. Application Data

(63) Continuation of application No. PCT/JP2015/069932, filed on Jul. 10, 2015.

(51) Int. Cl.
*A61B 90/00* (2016.01)
*A61B 1/00* (2006.01)
(Continued)

(52) U.S. Cl.
CPC ...... *A61B 1/00055* (2013.01); *A61B 1/00004* (2013.01); *A61B 1/005* (2013.01);
(Continued)

(58) Field of Classification Search
CPC combination set(s) only.
See application file for complete search history.

(56) References Cited

U.S. PATENT DOCUMENTS 4,329,980 A * 5/1982 Terada ............... A61B 1/00078
600/140
5,018,509 A * 5/1991 Suzuki ................ A61B 1/0005
348/65
(Continued)

FOREIGN PATENT DOCUMENTS

JP       S61-37931 B2    8/1986
JP       H03-198828 A    8/1991
(Continued)

OTHER PUBLICATIONS

Japanese Office Action dated Oct. 2, 2018 in Japanese Patent Application No. 2017-528016.
(Continued)

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

One embodiment of the present invention is a flexible tube insertion apparatus including a flexible insertion section to be inserted into a subject. The flexible tube insertion apparatus includes an insertion section state detecting device that detects a state of the insertion section necessary for insertion prediction as detection information when the insertion section is inserted into a subject, and at least one circuit that predicts, using the detection information detected by the insertion section state detecting device, a propulsion state of a distal end of the insertion section and a state of the subject when the insertion section is further inserted from the state of the insertion section, and produces an output based on the prediction.

8 Claims, 12 Drawing Sheets

(51) Int. Cl.
*A61B 1/005* (2006.01)
*A61B 5/06* (2006.01)

(52) U.S. Cl.
CPC ...... *A61B 1/00045* (2013.01); *A61B 1/00147* (2013.01); *A61B 5/065* (2013.01); *A61B 2090/064* (2016.02); *A61B 2090/065* (2016.02); *A61B 2562/0261* (2013.01)

(56) References Cited

U.S. PATENT DOCUMENTS

| | | | | |
|---|---|---|---|---|
| 5,482,029 | A * | 1/1996 | Sekiguchi | A61B 1/00039 600/109 |
| 6,468,203 | B2 * | 10/2002 | Belson | A61B 1/0053 600/146 |
| 6,858,005 | B2 * | 2/2005 | Ohline | A61B 1/0053 600/139 |
| 8,317,746 | B2 * | 11/2012 | Sewell | A61B 34/30 604/95.04 |
| 9,629,595 | B2 * | 4/2017 | Walker | A61B 5/062 |
| 2002/0062062 | A1 * | 5/2002 | Belson | A61B 1/0053 600/146 |
| 2006/0253115 | A1 * | 11/2006 | Avitall | A61B 18/1492 606/41 |
| 2007/0021742 | A1 * | 1/2007 | Viswanathan | A61B 18/04 606/27 |
| 2007/0161856 | A1 * | 7/2007 | Belson | A61B 1/00151 600/114 |
| 2009/0326322 | A1 * | 12/2009 | Diolaiti | A61B 1/00039 600/112 |
| 2010/0168519 | A1 * | 7/2010 | Matsuo | A61B 1/00071 600/139 |
| 2011/0009698 | A1 * | 1/2011 | Ashida | A61B 1/00006 600/118 |
| 2012/0046522 | A1 * | 2/2012 | Naito | A61B 1/00006 600/118 |
| 2012/0130173 | A1 * | 5/2012 | Lutze | A61B 1/00071 600/146 |
| 2012/0289777 | A1 * | 11/2012 | Chopra | A61B 1/00009 600/109 |
| 2013/0178705 | A1 * | 7/2013 | Takeuchi | A61B 1/0052 600/144 |
| 2013/0204124 | A1 * | 8/2013 | Duindam | A61B 5/065 600/424 |
| 2013/0261392 | A1 * | 10/2013 | Yamamoto | G02B 23/2476 600/117 |
| 2013/0345514 | A1 * | 12/2013 | Manion | A61B 1/008 600/117 |
| 2014/0288525 | A1 * | 9/2014 | Fudaba | A61B 5/066 604/500 |
| 2015/0057575 | A1 * | 2/2015 | Tsusaka | A61B 1/0055 600/587 |
| 2015/0313547 | A1 * | 11/2015 | Quinn | A61B 5/6885 600/587 |
| 2016/0331434 | A1 * | 11/2016 | Phillips | A61B 34/20 |
| 2017/0231699 | A1 * | 8/2017 | Flexman | G01D 5/353 600/424 |

FOREIGN PATENT DOCUMENTS

| | | |
|---|---|---|
| JP | H06-070879 A | 3/1994 |
| JP | H06-181882 A | 7/1994 |
| JP | 2012-115521 A | 6/2012 |
| WO | WO 2013/065606 A1 | 5/2013 |

OTHER PUBLICATIONS

International Search Report dated Oct. 6, 2015 issued in PCT/JP2015/069932.
English translation of International Preliminary Report on Patentability dated Jan. 25, 2018 together with the Written Opinion received in related International Application No. PCT/JP2015/069932.

* cited by examiner

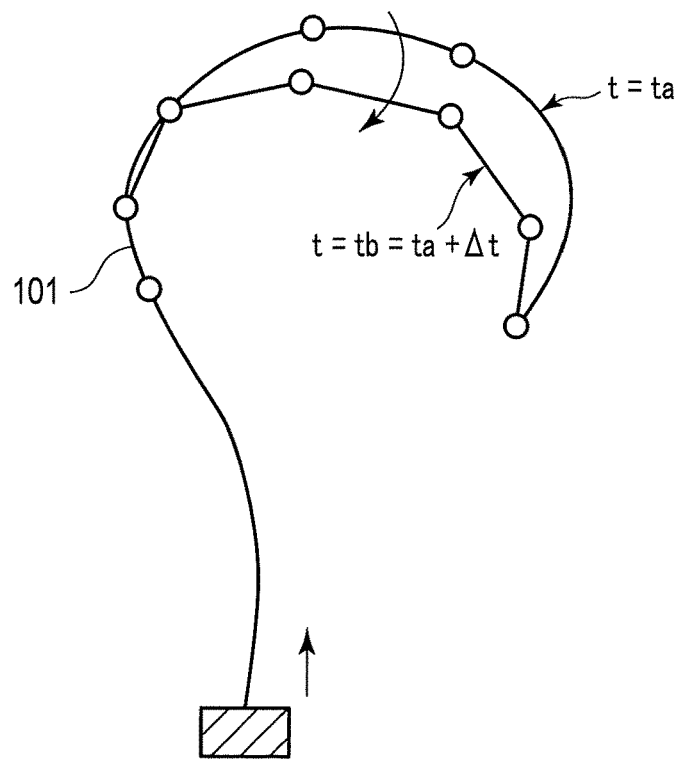
F I G. 7
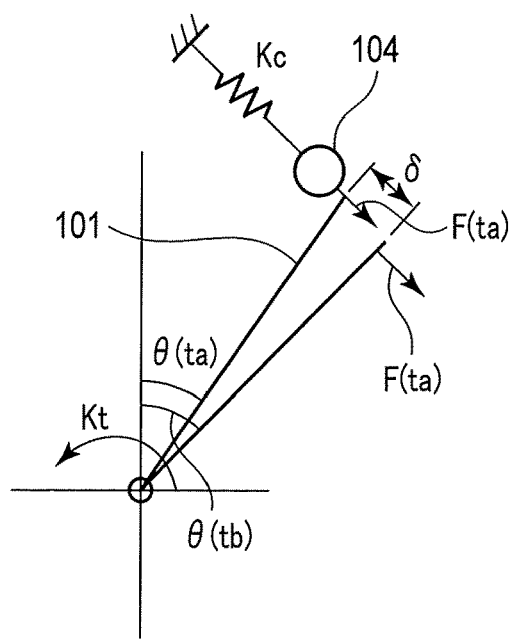
F I G. 8

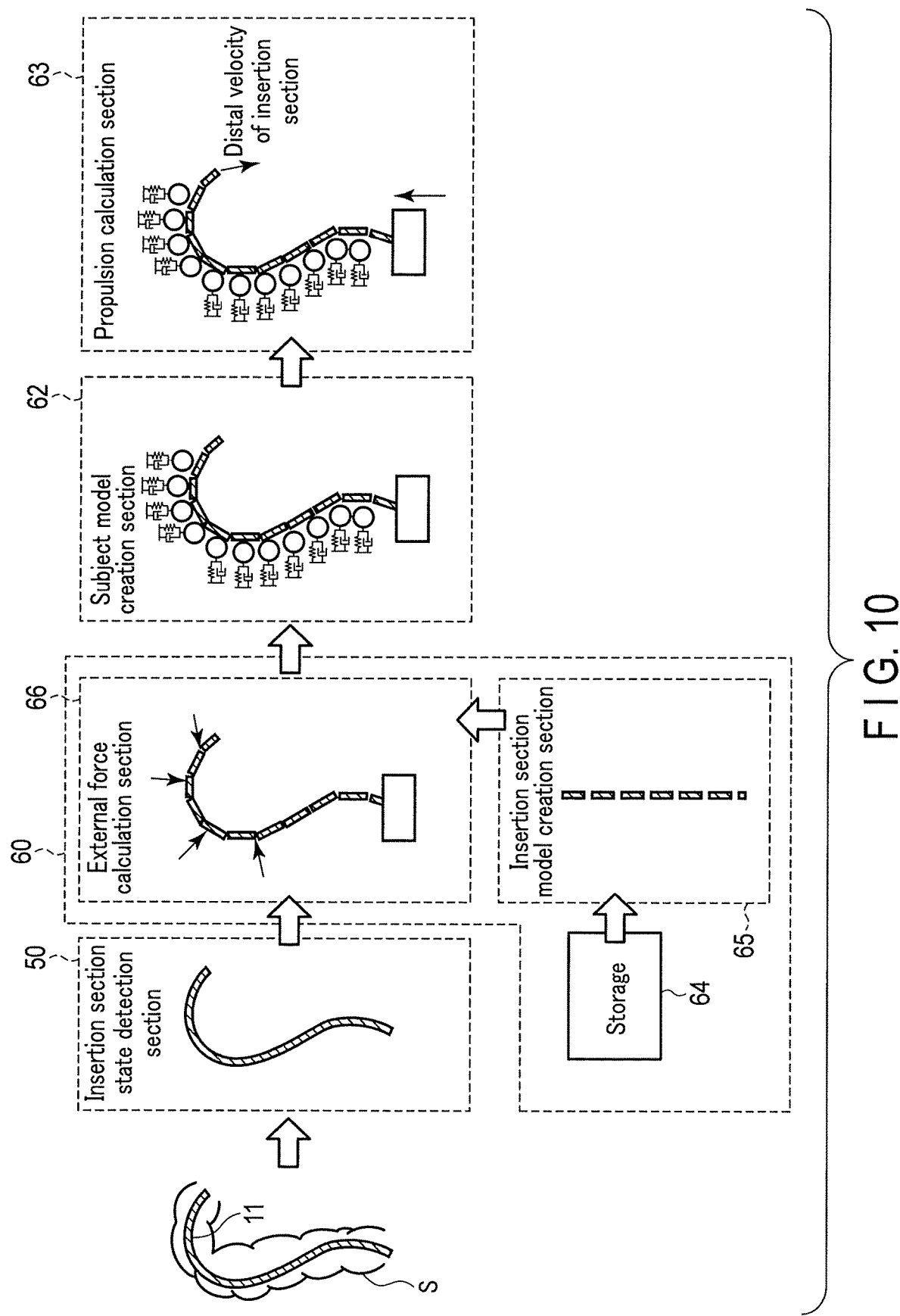
F I G. 10

Start of insertion    After insertion

| | A | B | C | D | E |
|---|---|---|---|---|---|
| Condition 1 | 0 | 0 | +10 | 0 | 0 |
| Condition 2 | 0 | 0 | 0 | +10 | 0 |
| Condition 3 | 0 | +10 | 0 | 0 | 0 |
| Condition 4 | 0 | 0 | 0 | +10 | +10 |

FLEXIBLE TUBE INSERTION APPARATUS COMPRISING INSERTION SECTION TO BE INSERTED INTO SUBJECT AND METHOD OF OPERATING THEREOF

CROSS-REFERENCE TO RELATED APPLICATIONS

This application is a Continuation Application of PCT Application No. PCT/JP2015/069932, filed Jul. 10, 2015, the entire contents of which are incorporated herein by references.

BACKGROUND OF THE INVENTION

1. Field of the Invention

The present invention relates to a flexible tube insertion apparatus comprising an insertion section to be inserted into a subject.

2. Description of the Related Art

In a flexible tube insertion apparatus, such as an endoscope apparatus comprising an insertion section to be inserted into a subject, it is known that the flexibility of the insertion section can be partially changed to improve the ease of insertion. For example, Jpn. Pat. Appln. KOKAI Publication No. 6-70879 discloses an endoscope apparatus that allows an operator to remotely select a portion of an insertion section whose flexibility is to be changed, in view of the flexibility patterns of the past insertions stored in a database. This improves the ease of insertion in an endoscopic examination (in particular, an colonoscopic examination). Jpn. Pat. Appln. KOKOKU Publication No. 61-37931 discloses an endoscope comprising an elongated insertion section divided into a plurality of areas as viewed in the longitudinal direction to allow the areas to have different levels of flexibility. Since the areas of the insertion section have different levels of flexibility, such an endoscope reduces the patient's distress during insertion and improves the ease of insertion.

BRIEF SUMMARY OF THE INVENTION

One embodiment of the present invention is a flexible tube insertion apparatus comprising a flexible insertion section to be inserted into a subject, an insertion section state detecting device that detects a state of the insertion section necessary for insertion prediction as detection information when the insertion section is inserted into a subject, and at least one circuit that predicts, using the detection information detected by the insertion section state detecting device, a propulsion state of a distal end of the insertion section and a state of the subject when the insertion section is further inserted from the state of the insertion section, and produces an output based on the prediction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 7 is a diagram schematically showing an insertion section model of an initial shape and an insertion section model after $\Delta t$ seconds.

FIG. 8 is a diagram illustrating a basic principle by which a subject model creation section calculates a stiffness value of a subject.

FIG. 10 is a diagram showing a flow of the insertion prediction in an example in which the insertion section is expressed in an articulated link model and the subject is expressed in a spring-mass model.

DETAILED DESCRIPTION OF THE INVENTION

Figure 1:
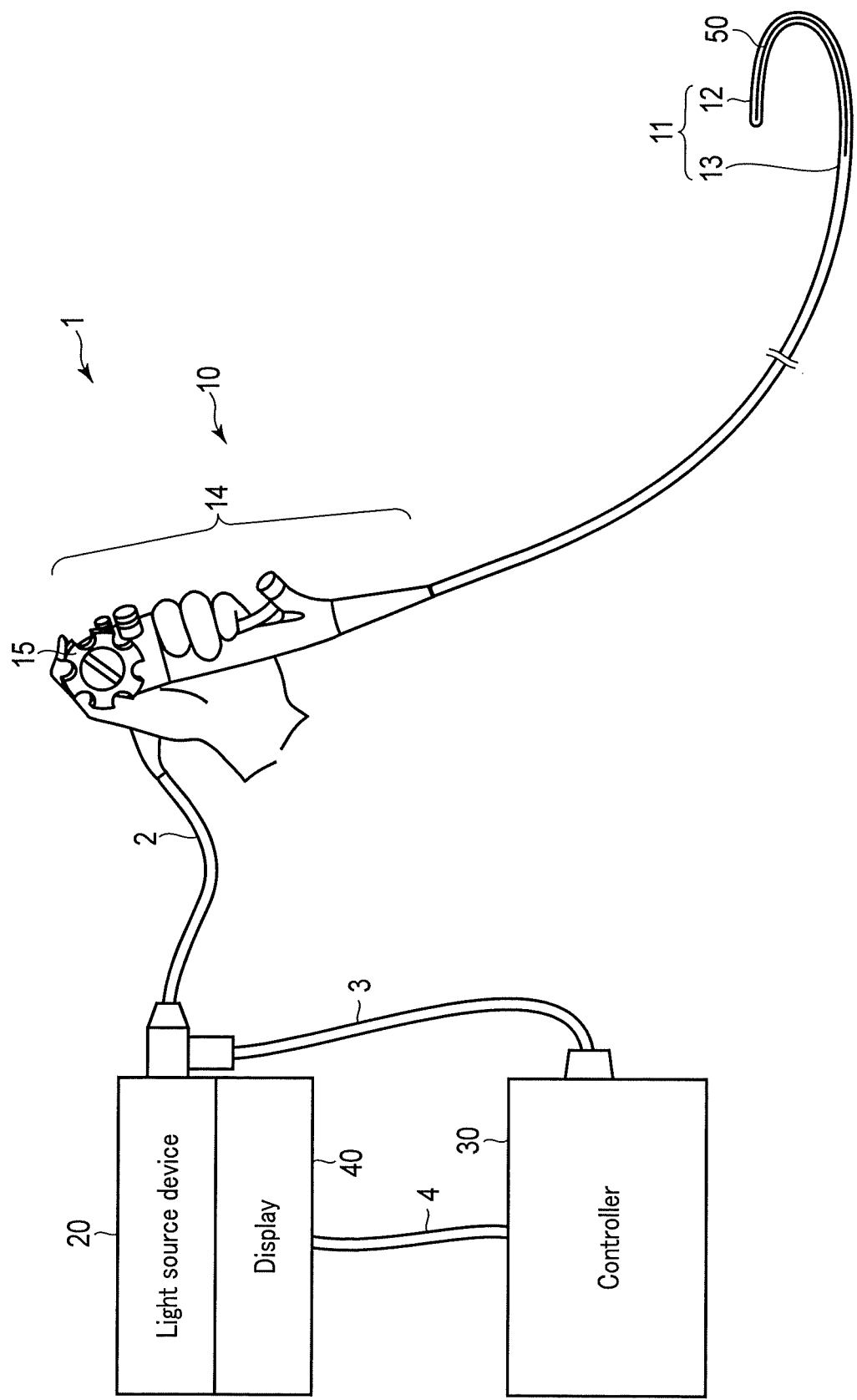
FIG. 1 is a diagram schematically showing a configuration of an endoscope apparatus.

FIG. 1 is a diagram schematically showing a configuration of an endoscope apparatus 1, which is a flexible tube insertion apparatus. The endoscope apparatus 1 comprises an endoscope 10, a light source device 20, a controller 30, and a display 40.

The endoscope 10 comprises a tubular insertion section 11 to be inserted into a subject, and an operation section 14 located proximal to the insertion section 11. The endoscope 10 is, for example, a colonoscope, and the subject is a large intestine. The insertion section 11 includes a distal portion 12 and a flexible tube portion 13 located proximal to the distal portion 12. The distal portion 12 incorporates, for example, an illumination optical system (illumination window), an observation optical system, and an image sensor, which are not shown in the drawings. The distal portion 12 includes a bending portion that is bent by a bending operation of the operation section 14. The flexible tube portion 13 is an elongated tube that is bendable and flexible. The operation section 14 is a portion of the endoscope 10 that is gripped by an operator. The operation section 14 includes an angle knob 15 used for a bending operation of the bending portion of the distal portion 12. When the operator operates the angle knob 15, the bending portion is bent in a given direction.

The endoscope 10 is connected to the light source device 20 via a universal cord 2 extending proximally from the operation section 14. The universal cord 2 includes a light guide (optical fiber) connected to the illumination optical system, an electric cable connected to the image sensor, and the like. The light source device 20 emits illumination light, and the emitted illumination light guides a light guide, and is applied to the subject through the illumination window of the distal portion 12.

The controller 30 is configured by a device including a CPU, and the like. The controller 30 is connected to the electric cable in the universal cord 2 via a cable 3, and thereby connected to the endoscope 10. The controller 30 is also connected to the display 40 via a cable 4.

The insertion section 11 includes at least a part of the insertion section state detection section 50 configured to detect the state of the insertion section 11 when the insertion section 11 is inserted into a subject. The insertion section state detection section 50 is a curved-shape detection sensor configured to detect a bending shape of, for example, the insertion section 11. Hereinafter, the insertion section state detection section 50, which is a magnetic sensor, will be explained as an example.

Figure 2:
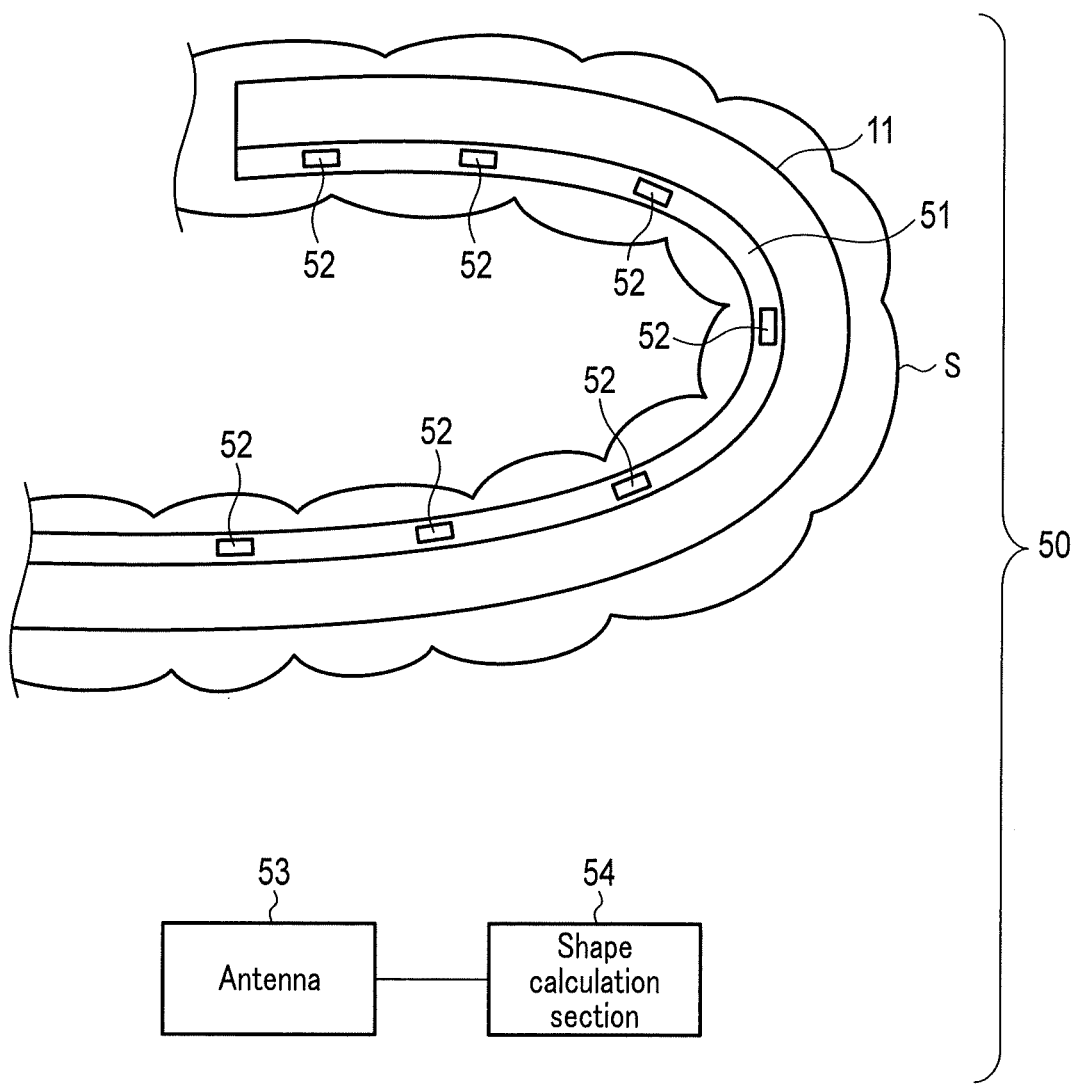
FIG. 2 is a diagram schematically showing an example of an insertion section state detection section.

FIG. 2 is a diagram schematically showing an example of the insertion section state detection section 50. The insertion section state detection section 50 includes an elongated probe 51 provided inside the insertion section 11. In the probe 51, a plurality of source coils 52 are provided to generate a magnetic field. The source coils 52 are arranged at intervals along the longitudinal axis direction of the insertion section 11. The insertion section state detection section 50 includes an antenna 53 configured to detect the magnetic field generated by the source coils 52. The antenna 53 is separate from the endoscope 10, and is arranged in the periphery of an intestinal tract S, which is a subject into which the endoscope 10 is inserted. Furthermore, the insertion section state detection section 50 includes a shape calculation section 54 configured to calculate a bending shape of the insertion section 11 on the basis of the magnetic field detected by the antenna 53. The shape calculation section 54 is also separate from the endoscope 10, and is provided in, for example, the controller 30.

The probe 51 is connected to, for example, the controller 30, and an alternating-current signal is applied to the source coils 52 from an alternating-current signal output section, not shown, of the controller 30. The antenna 53 detects the magnetic field generated by the source coils 52 and transmits a detection signal to the shape calculation section 54. The shape calculation section 54 calculates a bending shape of the insertion section 11 on the basis of the received detection signal. In this manner, the insertion section state detection section 50 detects the bending shape of the insertion section 11 inserted into the intestinal tract S.

The insertion section state detection section 50 is not limited to an insertion section shape detection section configured to detect the bending shape of the insertion section 11, and may be a known insertion section strain detection section configured to detect a bend or a strain of the insertion section 11, a known insertion section contact force detection section configured to detect a contact force of the insertion section 11 against the subject, or an insertion section state detection section that combines two or more of such sections.

Figure 3:
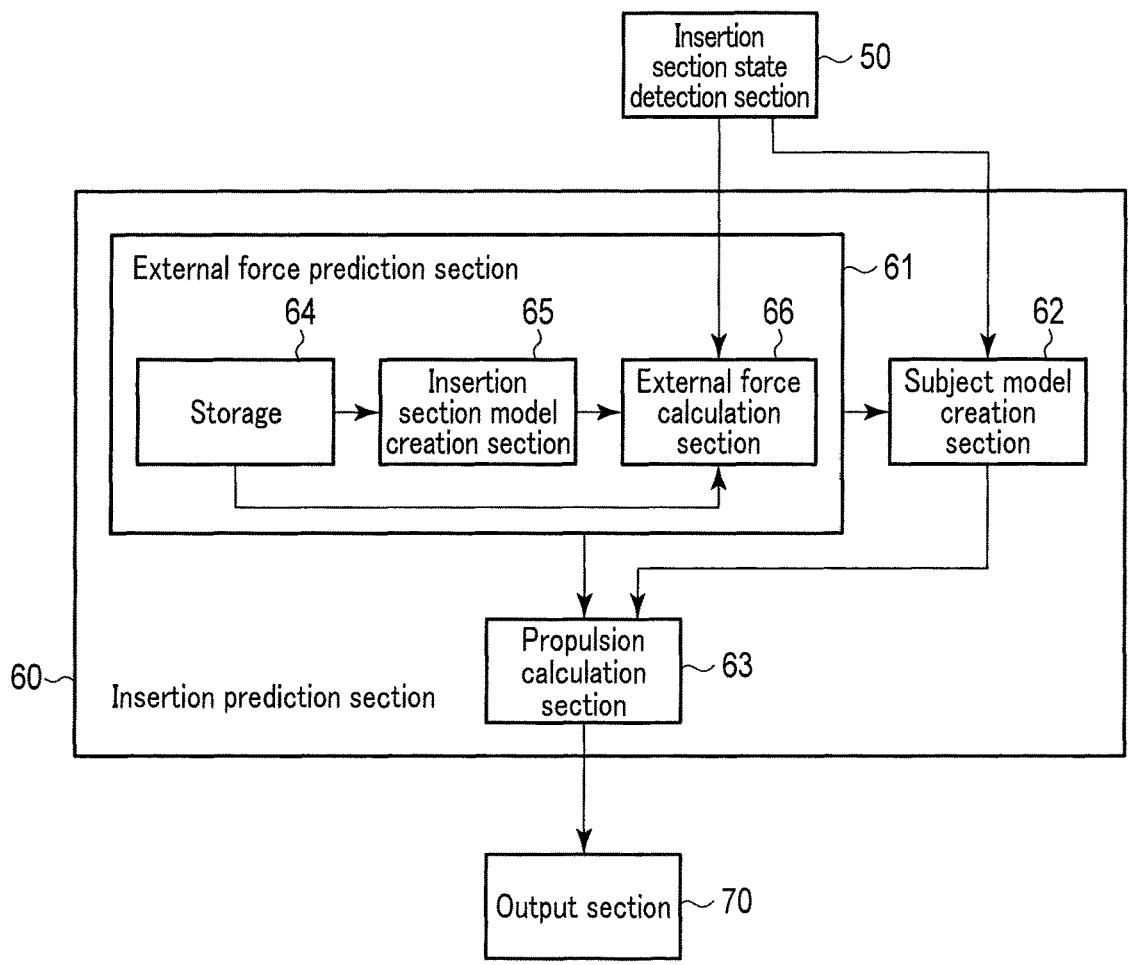
FIG. 3 is a block diagram schematically showing a main configuration relating to an insertion prediction in the endoscope apparatus.

FIG. 3 is a block diagram schematically showing a main configuration of the endoscope apparatus 1 relating to insertion prediction. In the present embodiment, the endoscope apparatus 1 predicts a propulsion state of a distal end of the insertion section in real time, using information on the state of the insertion section 11 detected by the insertion section state detection section 50. The endoscope apparatus 1 includes the insertion section state detection section 50, an insertion prediction section 60, and an output section 70. Each of the insertion prediction section 60 and the output section 70 is a processor that includes at least one circuit embedded in, for example, the controller 30, but may be separate from the controller 30. The insertion prediction section 60 predicts, in real time, a propulsion state of the distal end of the insertion section 11 and the state of the subject when the insertion section 11 is further inserted into the subject from the present state (the detection state detected by the insertion section state detection section 50), using information (e.g., the present bending shape information of the insertion section 11) necessary for insertion prediction obtained by the insertion section state detection section 50. The output section 70 produces an output on the basis of prediction obtained from the insertion prediction section 60. The output section 70 produces an output to change the state (e.g., the bending stiffness, weight distribution, and frictional force) of the insertion section 11 on the basis of, for example, the prediction of the propulsion state of the distal end of the insertion section 11.

The insertion prediction section 60 includes an external force prediction section 61, a subject model creation section 62, and a propulsion calculation section 63. An external force prediction section 61 estimates (calculates) an external force applied to the insertion section 11 on the basis of, for example, information necessary for insertion prediction obtained by the insertion section state detection section 50. The subject model creation section 62 creates a calculation model (subject model) of the subject on the basis of information obtained by the insertion section state detection section 50 and information on the external force estimated by the external force prediction section 61. The propulsion calculation section 63 performs prediction calculation of the propulsion state of the distal end of the insertion section using the information on the external force estimated by the external force prediction section 61 and the subject model created by the subject model creation section 62.

The external force prediction section 61 will be explained in more detail below. The external force prediction section 61 includes a storage 64, an insertion section model creation section 65, and an external force calculation section 66.

The storage 64 stores values relating to viscoelasticity of the insertion section 11, such as a value of rotational elasticity Kt and a value of rotational viscosity Ct, for each model or individual of the endoscope 10. The storage 64 also stores a bending stiffness value of the insertion section 11. These values stored in the storage 64 are read in the insertion section model creation section 65 and the external force calculation section 66. The storage 64 may be a storage medium separate from the controller 30.

The insertion section model creation section 65 creates a model (insertion section model) of the insertion section 11 on the basis of the information read from the storage 64. The insertion section model creation section 65 creates an insertion section model by modeling the insertion section 11 with a mechanical equation using an articulated link model 100, in which a plurality of rigid body links 101 are coupled, as a parallel arrangement (Voigt model) of springs 102 of a value of rotational elasticity Kt and dashpots 103 of a value of rotational viscosity Ct, as shown for example in FIG. 4. The value of rotational elasticity Kt and the value of rotational viscosity Ct are read from the storage 64. Alternatively, the insertion section model creation section 65 may express the insertion section 11 in a Finite Element Method (FEM) model, or may be expressed in a continuum-mechanical equation.

The external force calculation section 66 calculates an external force applied to the insertion section 11 from the subject, using the information obtained by the insertion section state detection section 50, the information read from the storage 64, and the insertion section model created by the insertion section model creation section 65. The external force is calculated according to Hooke's law, on the basis of, for example, the bending shape (bending angle) of the insertion section 11 and the bending stiffness value of the insertion section 11. The bending shape of the insertion section 11 is obtained by the insertion section state detection section 50, and the bending stiffness value of the insertion section 11 is read from the storage 64. The external force calculation section 66 calculates an external force applied to the insertion section 11 in real time.

Figure 5:
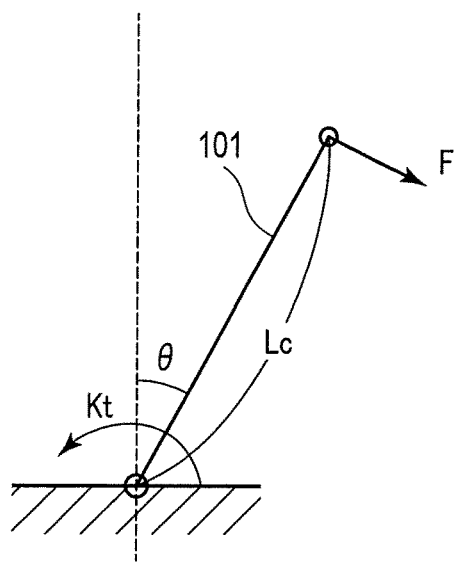
FIG. 5 is a diagram illustrating a basic principle by which an external force calculation section calculates an external force.

The basic principle by which the external force calculation section 66 obtains an external force is shown in FIG. 5, as an example of one rigid body link 101. Given that the force (the force component of the external force) applied to one rigid body link 101 in a direction vertical to the rigid body link 101 is $F_i$, the bending stiffness value of the rigid body link 101 is Kt, the bending angle is θ, and the link length is Lc, the following equations are satisfied.

$$F_i \cdot Lc = Kt \cdot \theta$$

$$F_i = Kt \cdot \theta / Lc$$

Figure 4:
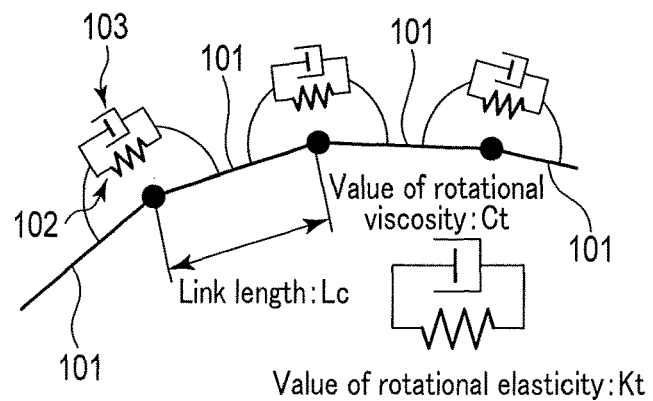
FIG. 4 is a diagram schematically showing an example of an insertion section model created by an insertion section model creation section.
Figure 6:
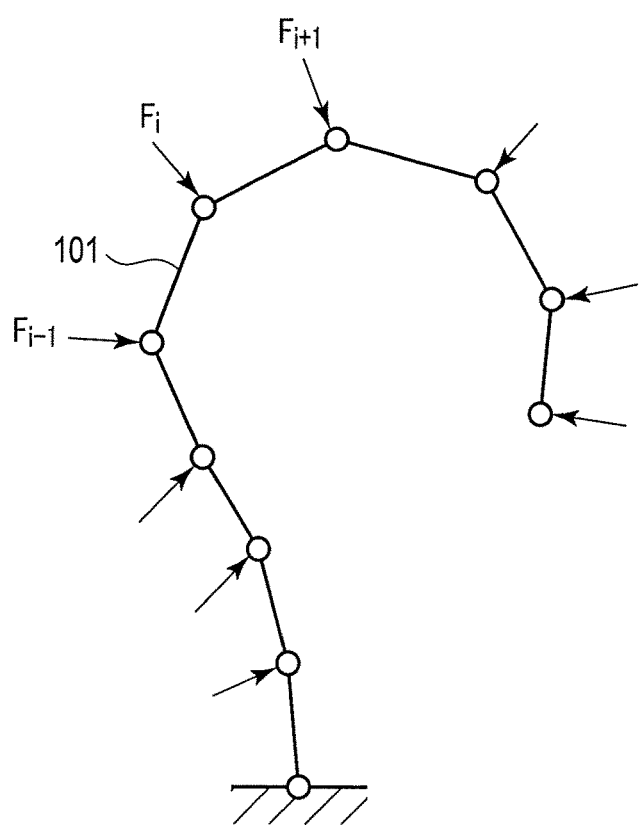
FIG. 6 is a diagram illustrating a basic principle by which an external force calculation section calculates an external force.

By applying this basic principle to the articulated link model 100 shown in FIG. 4, the external force F applied to the insertion section 11 is obtained. FIG. 6 is a diagram schematically showing an example of a force component $F_i$ of an external force applied to each rigid body link 101 in the articulated link model 100. The external force F may be obtained by the mechanical equation of the articulated link model 100, or may be obtained by, for example, a numerical analysis (convergence calculation) of the mechanical equation of the articulated link model 100, a numerical analysis (convergence calculation) based on a created Finite Element Method (FEM) model of the insertion section 11, or a continuum-mechanical equation.

When the insertion section strain detection section or the insertion section contact force detection section are adopted as the insertion section state detection section 50, the external force applied to the insertion section 11 is obtained from the insertion section state detection section 50. In such a case, calculation of the external force by the external force calculation section 66 may be omitted.

The subject model creation section 62 creates a calculation model of the subject on the basis of the information obtained by the insertion section state detection section 50 and the external force calculated from the external force prediction section 61. Hereinafter, assuming that the subject is a large intestine, an example in which the subject model creation section 62 creates a large intestine model will be explained. Here, the creation of the large intestine model means creation of an initial shape of the large intestine model and calculation of a stiffness value of the large intestine.

The subject model creation section 62 creates a large intestine model of the initial shape that is along the present bending shape of the insertion section 11 detected by the insertion section state detection section 50. Furthermore, as shown in FIG. 7, the subject model creation section 62 calculates a stiffness value Kc of the large intestine according to Hooke's law, on the basis of an insertion section model of the initial shape, in which the insertion section model created by the insertion section model creation section 65 is in the present bending shape of the insertion section 11 detected by the insertion section state detection section 50, a shape change (a relative bending amount) from the initial shape of the insertion section model after Δt seconds during which the insertion section 11 is further inserted into the large intestine, and an external force calculated by the external force calculation section 66.

The basic principle by which the subject model creation section 62 obtains a stiffness value Kc of the large intestine is shown in FIG. 8, as an example of one rigid body link 101. Let us assume that the initial time is ta, and that the time after Δt seconds during which the insertion section 11 is inserted into the large intestine is tb=ta+Δt. Let us assume that the link angle at the time ta is θ(ta), and the link angle at the time tb is θ(tb). Let us assume that the distance traveled by a mass point 104 that contacts the rigid body link 101 at its distal end during the period of Δt seconds is δ. The insertion section state detection section 50 detects the state of the insertion section 11, such as the bending shape, at least at the time ta and the time tb, and the subject model creation section 62 obtains information about the detection state at the times ta and tb from the insertion section state detection section 50.

The link angle θ and the distance δ when the time changes from ta to tb are known from the information about the detection state by the insertion section state detection section 50. The link length Lc, which is defined to create an insertion section model at the insertion section model creation section 65, is also known. The bending stiffness value Kt of the rigid body link 101 (which is determined according to the model and read from the storage 64) is also known. Accordingly, the stiffness value Kc of the large intestine, which is an unknown parameter, is calculated by the following equations:

$$F(tb) = Kt \cdot \theta(tb)/Lc$$

$$Kt\{\theta(tb) - \theta(ta)\}/Lc = F_i(tb) = Kc \cdot \delta$$

$$Kc = Kt\{\theta(tb) - \theta(ta)\}/\delta \cdot Lc$$

By applying this basic principle to the articulated link model 100, the stiffness value Kc of the large intestine can be directly obtained by the mechanical equations of the articulated link model 100 and the large intestine model. The stiffness value Kc of the large intestine may be obtained directly from the mechanical equations of the articulated link model 100 and the large intestine model, or may be obtained by, for example, a numerical analysis (convergence calculation) of the mechanical equations of the articulated link model 100 and the large intestine, a numerical analysis (convergence calculation) based on created FEM models of the insertion section 11 and the large intestine, or a continuum-mechanical equation.

The propulsion calculation section 63 performs an insertion simulation using information prepared by the external force prediction section 61 and the subject model creation section 62, and predicts a propulsion state of the distal end of the insertion section. That is, the propulsion calculation section 63 calculates a propulsion state of the distal end of the insertion section when the insertion section 11 is further inserted from the present state, namely, the future propulsion state, using the insertion section model created by the insertion section model creation section 65 and the subject model (large intestine model) created by the subject model creation section 62 in combination. Here, the propulsion state refers to a relative velocity, a relative position, or both of the insertion section model relative to the large intestine model. The calculation of the propulsion state is performed in real time by the propulsion calculation section 63.

The insertion prediction section 60 may be an insertion prediction section that is a combination of a calculation prediction section that predicts a propulsion state of the distal end of the insertion section 11 by calculating the state of the insertion section 11 and the state of the subject, and a history prediction section that predicts the state of the insertion section 11 and the state of the subject from an insertion pattern created based on the past data of insertion of the insertion section 11 into a subject. In this case, the state of the insertion section 11 and the state of the subject are predicted using the storage 64 in which the past insertion data is stored, and the external force prediction section 61, the subject model creation section 62, and the propulsion calculation section 63 perform calculation of an external force, creation of a subject model, and a propulsion calculation, using the information obtained by the insertion section state detection section 50.

Figure 9:
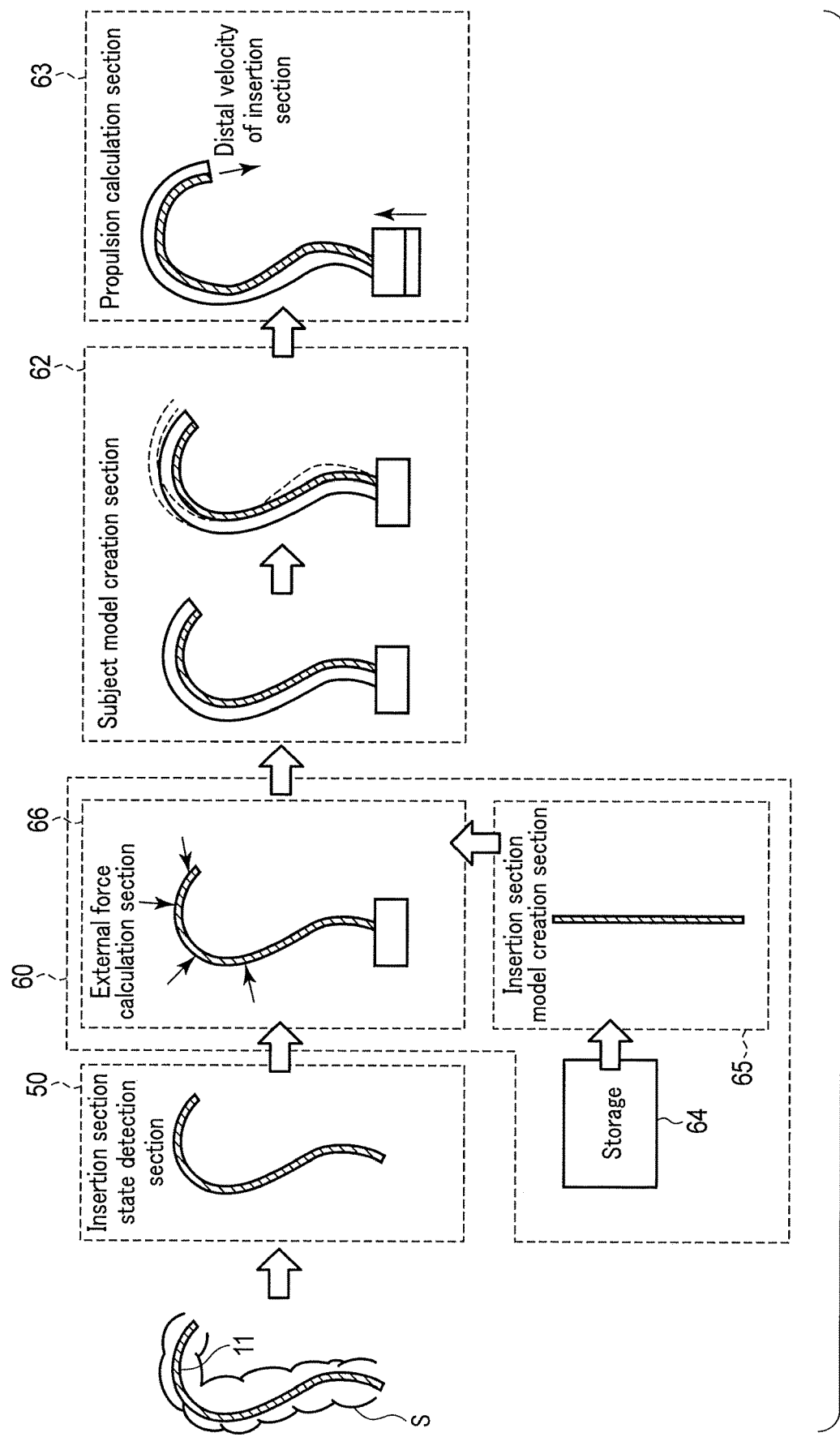
FIG. 9 is a diagram showing a flow of the insertion prediction in an endoscope apparatus.

FIG. 9 is a diagram showing a flow of insertion prediction in the endoscope apparatus 1. FIG. 10 is a diagram showing a flow of insertion prediction in an example in which the insertion section 11 is expressed in an articulated link model 100, and the large intestine, which is the subject, is expressed in a spring-mass model.

The insertion section 11 of the endoscope 10 is inserted into an intestinal tract by an operator. The insertion section 11 passes through the intestinal tract while bending to follow the shape inside of the intestinal tract. An optical image of the subject obtained by the observation optical system on a distal face of the distal portion 12 is converted into an electric signal by an image sensor, and output to the controller 30. The controller 30 causes an image processing section, not shown, to generate an image signal of the subject on the basis of the output electric signal. On the basis of the generated image signal, an image of the subject is displayed on the display 40.

During insertion of the insertion section 11 into the intestinal tract, the insertion section state detection section 50 detects the state (e.g., the bending shape) of the insertion section 11 in real time. The insertion section model creation section 65 creates an insertion section model on the basis of information read from the storage 64. The external force calculation section 66 obtains an external force F by which the insertion section model becomes the bending shape of the insertion section 11 obtained by the insertion section state detection section 50, using the information read from the storage 64 and the insertion section model created by the insertion section model creation section 65.

The subject model creation section 62 creates a subject model of the initial shape that is along the bending shape of the insertion section 11 obtained by the insertion section state detection section 50. The subject model of the initial shape is a discretized large intestine model including a finite number of contact points, as shown for example in FIG. 10. Furthermore, the subject model creation section 62 obtains a stiffness value Kc of the intestinal tract from the initial bending shape of the insertion section 11 (at a certain time), the bending shape of the insertion section 11 after $\Delta t$ seconds during which the insertion section 11 is inserted into the large intestine, and an external force obtained by the external force calculation section 66. Thereby, a subject model is created.

The propulsion calculation section 63 simulates insertion of the insertion section 11 at a time after the time $\Delta t$, using the insertion section model and the subject model, and predicts a propulsion state of the distal end of the insertion section, for example, a relative velocity of the distal end of the insertion section.

Figure 11:
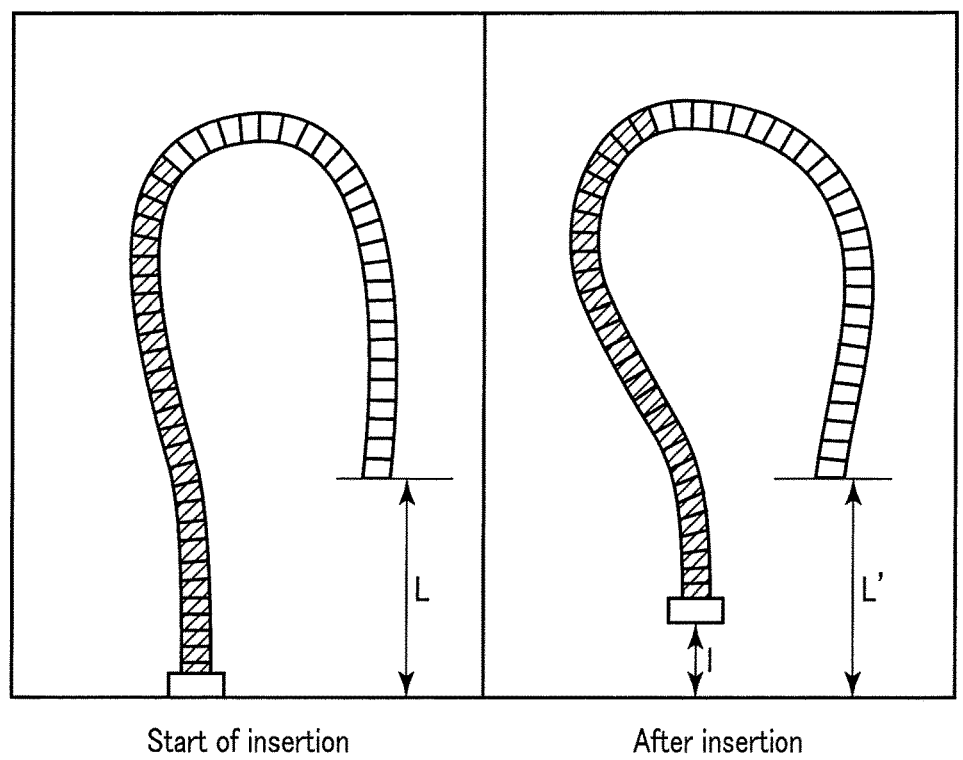
FIG. 11 is a diagram showing an example of a calculation result of a state of the insertion section calculated by an insertion prediction section.

FIG. 11 shows an example of a simulation result of the state of the insertion section 11 calculated by the insertion prediction section 60. As can be seen therefrom, the base (proximal) side of the insertion section 11 that continues to be inserted will be further bent, as compared to the state before the insertion is started (present state). That is, it can be seen that the distal movement amount remains unchanged by insertion by an insertion amount 1 (L=L'), and that the insertion section 11 is bent without causing the distal end of the insertion section 11 (without generating a velocity) to advance when the base side of the insertion section 11 is advanced. In this case, the propulsion calculation section 63 predicts that the relative velocity of the distal end of the insertion section is reduced. That is, when the operator keeps inserting the insertion section 11 into the large intestine, the insertion force will not be properly transmitted to the distal end of the insertion section 11, thus preventing smooth insertion of the insertion section 11.

Accordingly, the endoscope apparatus 1 changes the state of the insertion section 11 according to an output from the output section 70, to allow a smooth insertion operation of the insertion section 11 in an intestinal tract. Hereinafter, various aspects of the output section 70 will be explained.

Figure 12:
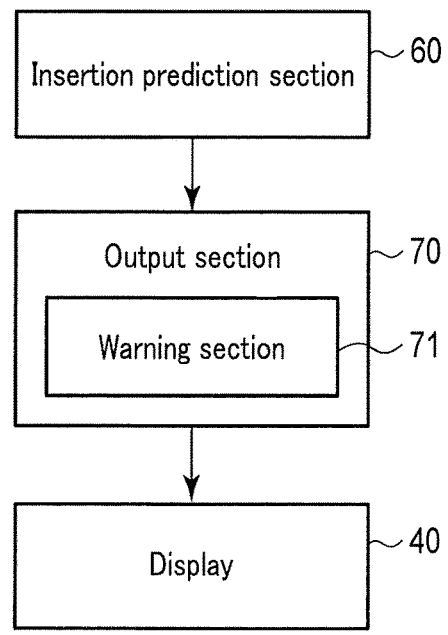
FIG. 12 is a block diagram schematically showing an output section and peripherals according to a first aspect.

FIG. 12 is a block diagram schematically showing the output section 70 and peripherals according to a first aspect. The output section 70 includes a warning section 71. When the insertion prediction section 60 predicts that the relative velocity of the distal end of the insertion section 11 is reduced to, for example, a value less than a predetermined value, namely, that the insertion section 11 would become stuck in a flexure such as the sigmoid colon by further insertion, the warning section 71 outputs a warning to inform the operator of this. That is, the warning section 71 plays a role of informing the operator of the prediction result of the propulsion state in the insertion prediction section 60.

In the first aspect, the warning section 71 is connected to, for example, the display 40, and a warning is displayed on the display 40 by means of characters, an image, or blinking on the basis of an output from the warning section 71. That is, when it is predicted that the distal end of the insertion section 11 would not advance by further insertion of the insertion section 11 from the present state, namely, when the insertion prediction section 60 predicts that the insertion section 11 would be in a stuck state with no propulsion force at its distal end, the warning section 71 outputs a warning to the operator who attempts to further insert the insertion section 11. The warning to be displayed may be a message indicating that extension may occur due to the stuck state, such as "further insertion may extend the intestinal tract", or a message recommending that the insertion operation should be discontinued, or that the insertion section should be pulled back, such as "discontinuation of insertion is recommended", or "pullback is recommended". The warning section 71 may inform the operator of the warning by making a sound such as a warning sound or a message sound, in addition to, or instead of, the display on the display 40.

Figure 13:
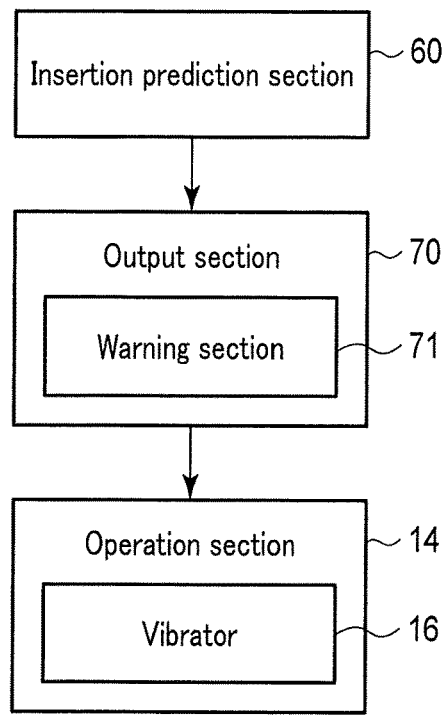
FIG. 13 is a block diagram schematically showing an output section and peripherals according to a second aspect.

FIG. 13 is a block diagram schematically showing the output section 70 and periferals according to a second aspect. The output section 70 includes a warning section 71, as in the first aspect. In the present aspect, a vibrator 16 embedded in or externally attached to the operation section 14 in the endoscope 10 vibrates based on an output from the warning section 71. That is, the warning section 71 transmits, to the vibrator 16, a control signal to vibrate the vibrator 16, thus causing the vibrator 16 to vibrate. When this vibration is transmitted to the operator who grips the operation section 14, the operator senses the warning. It is desirable that this vibration has a vibration pattern different from vibration patterns that may occur during use of the endoscope 10, namely, a specific vibration pattern such as an intermittent vibration pattern, to inform the operator that the vibration is a warning. The warning by vibration of the vibrator 16 may be used in combination with at least one of the warning by display on the display 40 and the warning by a warning sound or a message sound.

Figure 14:
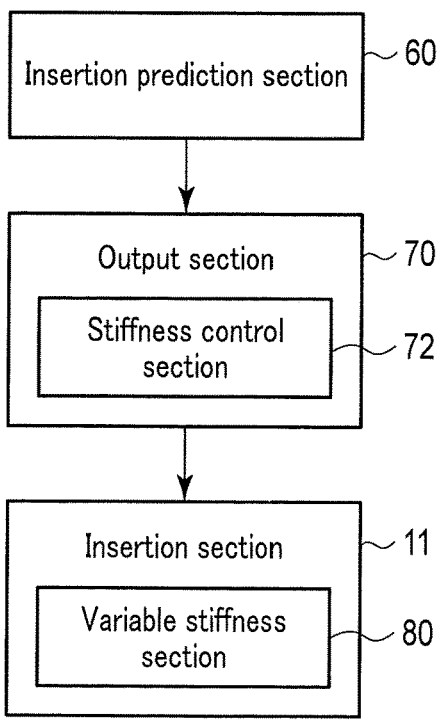
FIG. 14 is a block diagram schematically showing an output section and peripherals according to a third aspect.
Figures 15, 16:
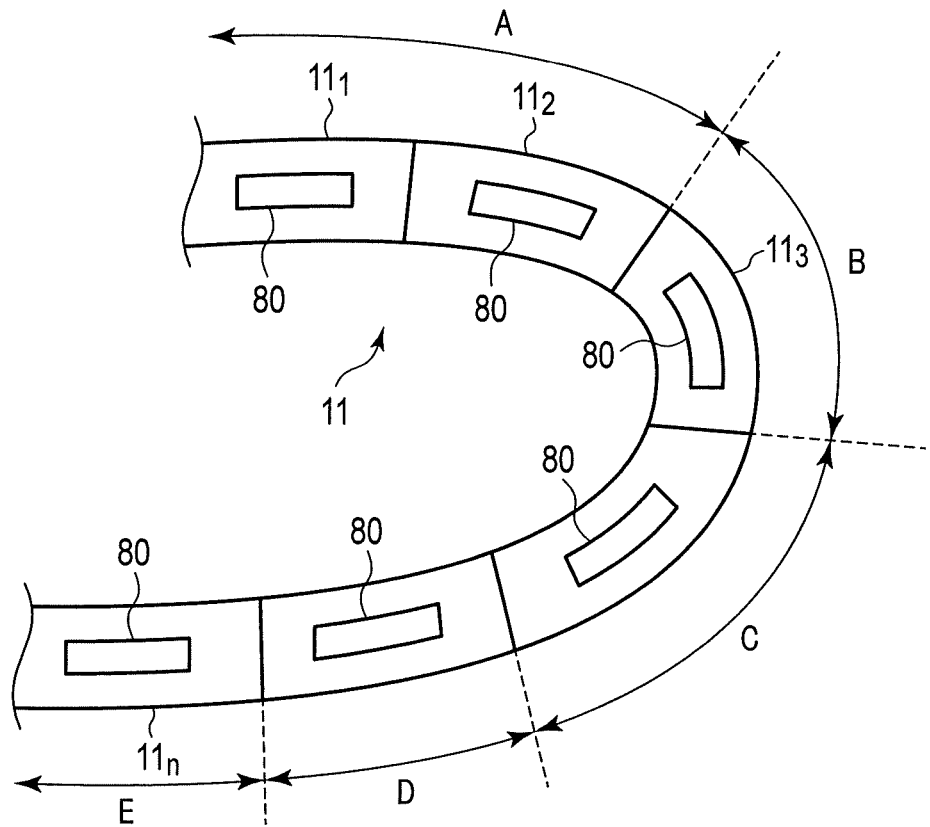
FIG. 15 is a diagram schematically showing an example of a variable stiffness section provided in the insertion section.
FIG. 16 is a diagram showing an example of a map created in bending stiffness control (automatic control) of the insertion section according to the third aspect.

FIG. 14 is a block diagram schematically showing an output section 70 and peripherals according to a third aspect. The output section 70 includes a stiffness control section 72 that performs control to change the bending stiffness of the insertion section 11. In the present aspect, the insertion section 11 includes a variable stiffness section 80, which is a variable stiffness actuator that allows the bending stiffness of the insertion section 11 to be changed on a segment-by-segment basis, as shown in FIG. 15. The variable stiffness section 80 is changed in bending stiffness by a control signal from the stiffness control section 72, namely, the stiffness control section 72 changes the bending stiffness of the insertion section 11. By changing the bending stiffness of the insertion section 11, it is possible to prevent the insertion section 11 from being stuck, thus allowing smooth insertion of the insertion section 11.

For convenience, let us assume that the insertion section 11 comprises a plurality of continuous segments (virtual units into which the insertion section 11 is evenly divided as viewed in the longitudinal direction) defined in the longitudinal axis direction thereof. In FIG. 15, segments $11_1$, $11_2$, $11_3$, . . . , and $11_n$ of the insertion section 11 are shown. A variable stiffness section 80 is provided in each of the segments. The variable stiffness section 80 is, for example, an Electroactive Polymer Artificial Muscle (EPAM) that changes its stiffness by extending and contracting according to an applied voltage, and its bending stiffness becomes higher as the applied voltage value increases. The variable stiffness section 80 is not limited thereto, and may be of any material that changes the bending stiffness of the insertion section 11 in response to a control signal from the stiffness control section 72.

An example of the bending stiffness control (automatic control) of the insertion section 11 performed by the output section 70 according to the third aspect will be explained. As shown in FIG. 15, the areas of the insertion section 11 whose bending stiffness is to be changed are set in advance on a segment-by-segment basis (e.g., areas A, B, C, D, and E). As shown in FIG. 16, a map that shows how the bending stiffness should be changed in each of the areas A-E is created in advance (e.g., Conditions 1, 2, 3, and 4). An insertion simulation is performed in the endoscope apparatus 1 according to the various conditions, and a condition under which the relative velocity of the distal end becomes the highest is determined from the propulsion calculation result of each of the conditions obtained by the insertion prediction section 60. On the basis of the determined condition, the stiffness control section 72 controls the bending stiffness of each of the variable stiffness sections 80, namely, the bending stiffness of each area of the insertion section 11.

Figure 17:
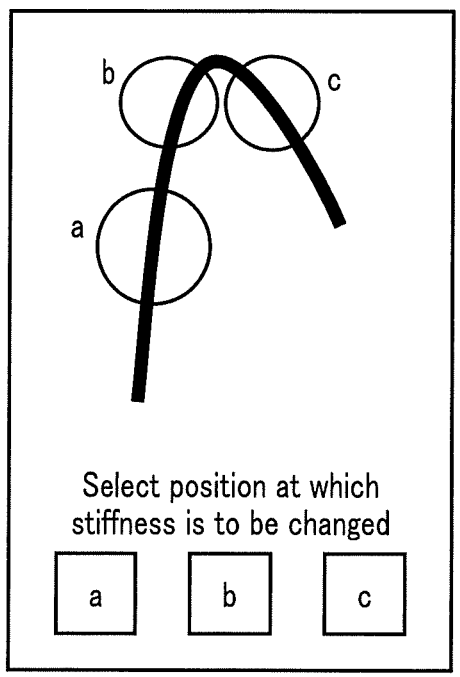
FIG. 17 is a diagram showing an example of a screen displayed on a display in bending stiffness control (manual control) of the insertion section according to the third aspect.

Another example of the bending stiffness control (manual control) of the insertion section 11 performed by the output section 70 according to the third aspect will be explained. When it is predicted that the distal end of the insertion section 11 would not advance during passage of the insertion section 11 through a flexure of the subject, a screen as shown in FIG. 17 is displayed on the display 40 (or a display separate therefrom) in accordance with the bending shape of the insertion section 11 obtained from the insertion section state detection section 50. It is preferable that the display on which such a screen is displayed is an input device such as a touch panel. By making an input to the screen displayed on the touch panel, the operator selects a position (stiffness change position) at which the bending stiffness of the insertion section 11 is to be changed.

In the example shown in FIG. 17, three positions are set in advance as the stiffness change positions, namely, the position a on the base side of the insertion section 11, the position b on the front side of the apex of the flexure of the subject, and the position c on the distal side of the insertion section 11. The operator can select one or more positions from these three positions.

Figure 18:
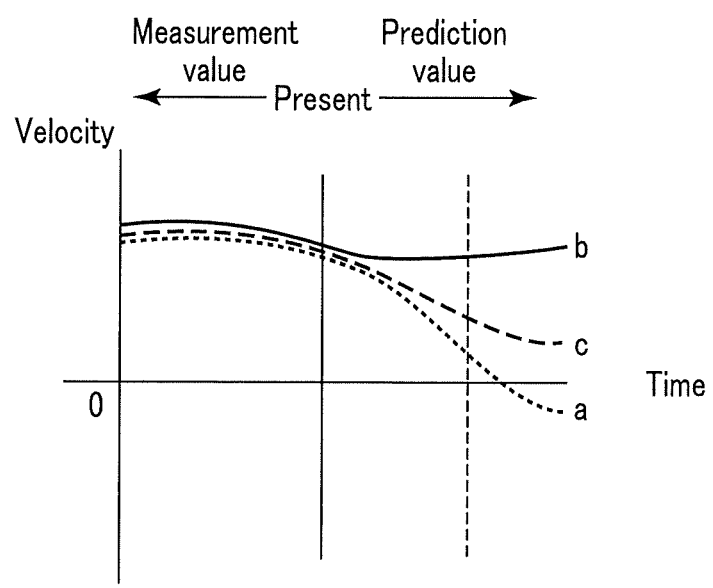
FIG. 18 is a diagram showing an example of prediction of a propulsion state of a distal end of the insertion section after a change in stiffness.

FIG. 18 shows an example of relative velocities of the distal end of the insertion section 11 predicted by the propulsion calculation section 63 before and after the change of the bending stiffness of the insertion section 11, which is caused by control of the bending stiffness value of the variable stiffness section 80 by the stiffness control section 72. It is predicted that the relative velocity of the distal end of the insertion section at the position a is gradually reduced from the present value, and eventually reaches zero or lower (i.e., the distal end of the insertion section does not advance and is pulled back). It is predicted that the relative velocity of the distal end of the insertion section at the position b remains substantially unchanged from the present value. It is predicted that the relative velocity of the distal end of the insertion section at the position c is gently reduced from the present value. On the basis of such predictions, it is seen that the relative velocity becomes the highest (the distal end of the insertion section advances most easily) at the position b. The operator may select the position c as the position to be transmitted to the variable stiffness section 80, or may select a position other than the position c based on the prediction result as well as experience. The operator may select one position, or two or three positions.

The stiffness change position is not limited to a position set in advance, and may be configured in such a manner that the bending stiffness of a given position (area) at which the operator has touched the touch panel changes. Furthermore, the stiffness change position may be smoothly moved using a finger (via a touch panel operation).

When a stiffness change position is selected, the stiffness change amount is set in such a manner that the bending stiffness value decreases by, for example, 10% at that position. By decreasing the bending stiffness at the stiffness change position, the insertion section 11 is easily bent, and is prevented from being stuck. Alternatively, a stiffness change amount of a given value may be input by the operator. Moreover, the bending stiffness may be changed by, for example, sliding a screen displayed on the display 40 (or a display separate therefrom).

As described above, the stiffness control section 72 is a state changing section configured to change the state of the insertion section 11, namely, the bending stiffness of each area of the insertion section 11 in this case, in such a manner that the distal end of the insertion section 11 is propelled when the distal end of the insertion section 11 is predicted to be stuck, on the basis of the prediction result of the propulsion state by the insertion prediction section 60.

Figure 19:
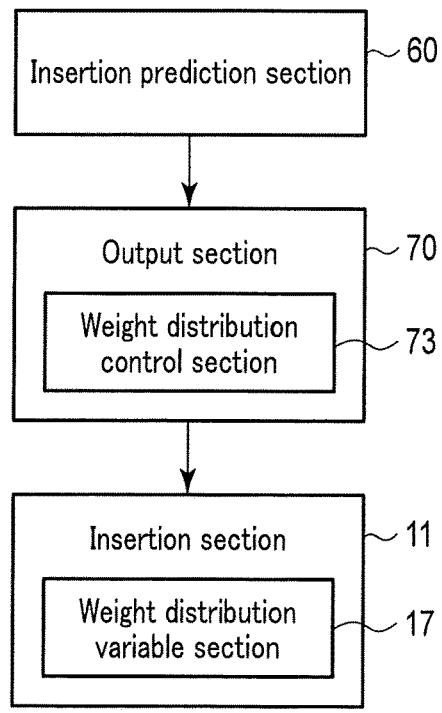
FIG. 19 is a block diagram schematically showing an output section and peripherals according to a fourth aspect.

FIG. 19 is a block diagram schematically showing the output section 70 and peripherals according to a fourth aspect. The output section 70 includes a weight distribution control section 73 that performs control to change the weight distribution of the insertion section 11. In the present aspect, the insertion section 11 includes a weight distribution variable section 17 configured to change the weight distribution of the insertion section 11. The weight distribution variable section 17 is controlled by the weight distribution control section 73.

The weight distribution variable section 17 is configured by a weight distribution varying member, which is, for example, a wire including a weight at its distal end, and is embedded in a channel tube, not shown, extending in the axial direction in the insertion section 11. The weight distribution variable section 17 changes the weight distribution of the insertion section 11 by moving the weight distribution varying member in the channel tube on the basis of the control by the weight distribution control section 73. For example, the weight distribution variable section 17 changes the weight distribution of the insertion section 11 so as to increase the weight distribution at the position which is predicted to be stuck (position at which the relative velocity becomes high), on the basis of the control by the weight distribution control section 73. This prevents the insertion section 11 from being stuck and allows smooth insertion of the insertion section 11.

As described above, the weight distribution control section 73 is a state changing section configured to change the state of the insertion section 11, namely, the weight distribution of the insertion section 11 in this case, so as to propel the distal end of the insertion section when the distal end of the insertion section is predicted to be stuck, on the basis of the prediction result of the propulsion state by the insertion prediction section 60.

The operation of the weight distribution variable section 17 is not limited to an operation automatically controlled by the weight distribution control section 73, and may be a manual operation. In this case, as in the first and second aspects, the output section 70 includes a warning section 71, and the operator who has sensed the warning (e.g., characters, sound, and vibration) issued by the warning section 71 manually moves the weight distribution variable section 17 to change the weight distribution of the insertion section 11.

Figure 20:
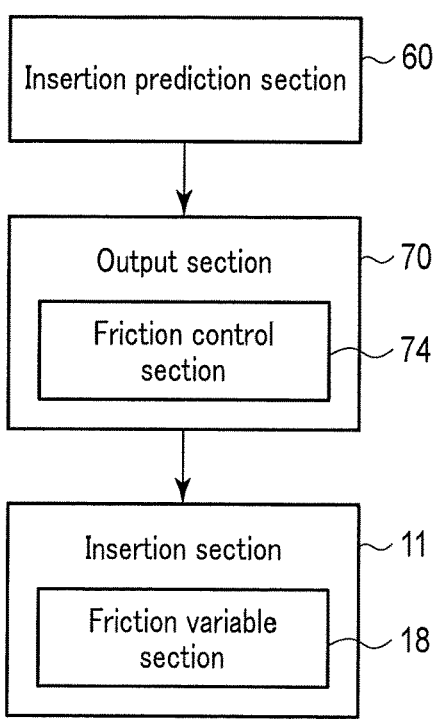
FIG. 20 is a block diagram schematically showing an output section and peripherals according to a fifth aspect.

FIG. 20 is a block diagram schematically showing the output section 70 and peripherals according to a fifth aspect. The output section 70 includes a friction control section 74 that performs control to change the frictional force of the insertion section 11. In the present aspect, the insertion section 11 includes a friction variable section 18 configured to change the frictional force of the insertion section 11. The friction variable section 18 is a vibration generator that applies vibration to the insertion section 11 using, for example, a vibration motor attached to the insertion section 11. Alternatively, the friction variable section 18 may be an air generator that ejects air from the insertion section 11 toward the outside. Driving of the friction variable section 18 is controlled by a friction control section 74.

The friction variable section 18 changes the friction of the insertion section 11 when driven under the control of the friction control section 74. For example, the friction variable section 18 vibrates the insertion section 11 or ejects air from the insertion section 11, so as to decrease the friction of the position that is predicted to be stuck (position having a high relative velocity), on the basis of the control by the friction control section 74. This decreases the frictional force between the insertion section 11 and the intestinal wall and allows the insertion section 11 to be easily inserted into a deep portion of the large intestine, thus allowing smooth insertion of the insertion section 11 while preventing the insertion section 11 from being stuck.

Thus, the friction control section 74 is a state changing section configured to change the state of the insertion section 11, namely, the frictional force of the insertion section 11 against the subject in this case, to propel the distal end of the insertion section when it is predicted that the distal end of the insertion section 11 would be stuck, on the basis of the prediction result of the propulsion state by the insertion prediction section 60. The operation of the friction variable section 18 is not limited to an operation automatically controlled by the friction control section 74, and may be a manual operation.

Thus, when the insertion prediction section 60 predicts that the insertion section 11 would not advance from the present state by further insertion by the operator, the output section 70 causes the stiffness control section 72, the weight distribution control section 73, or the friction control section 74 to control the state (e.g., the bending stiffness, the weight distribution, and the frictional force) of the insertion section 11 to advance the distal end of the insertion section to a deep portion of the large intestine, on the basis of the information (e.g., bending shape, strain, and contact force of the insertion section 11) obtained by the insertion section state detection section 50. The output section 70 may be a combination of two or more selected from the warning section 71, the stiffness control section 72, the weight distribution control section 73, and the friction control section 74.

Furthermore, the bending state of the insertion section 11 may be controlled by varying the bending angle of the insertion section 11 using the angle knob 15 provided in the operation section 14 as a state changing section.

As described above, according to the present embodiment, when the distal end of the insertion section 11 of the endoscope 10 passes through a flexure of a lumen such as a large intestine (intestinal tract), an insertion operation can be performed by confirming, based on insertion prediction by the insertion prediction section 60, the propulsion state of the distal end of the insertion section 11 (which advances, does not easily advance, or stops) when the insertion section 11 is further inserted (in the future) from the present state (at present). In particular, the insertion prediction in the present embodiment is a simulation performed by constructing both the insertion section model created by the insertion section model creation section 65 of the external force prediction section 61 and the subject model created by the subject model creation section 62, and is an accurate prediction of the actual insertion operation of the insertion section 11. Therefore, according to the present embodiment, it is possible to provide an endoscope apparatus 1 with an improved ease of insertion by the insertion prediction.

Moreover, according to the present embodiment, when it is predicted, based on the insertion prediction by the insertion prediction section 60, that the distal end of the insertion section 11 would stop by further insertion of the insertion section 11 (in the future), namely, the intestinal tract would extend by further insertion, it is possible to perform an operation to discontinue the insertion operation, or to pull back the insertion section 11 before the patient feels distress by the extension, by making an output from the warning section 71 of the output section 70. It is thereby possible to reduce the patient's distress caused by the extension.

Furthermore, when it is predicted that the insertion section 11 would stop, it is possible to cause the state changing section of the output section 70 to continuously advance the distal end of the insertion section, by controlling the state of the insertion section 11 (e.g., bending stiffness, weight distribution, or frictional force (contact force and contact angle between the subject and the insertion section)) to advance the distal end of the insertion section 11. It is thereby possible to smoothly insert the insertion section 11 while preventing the insertion section 11 from being stuck at a flexure of a lumen. Furthermore, the operator is allowed to drive the state changing section based on the insertion prediction by the insertion prediction section 60 as well as experience, and to take flexible measures to prevent the insertion section 11 from being stuck.

Thus, the endoscope apparatus 1 according to the present embodiment determines the propulsion state, the stiffness change position, or the position of the distal end of the insertion section not based only on the past or present state of the subject. According to the present embodiment, it is possible to provide an endoscope apparatus 1 that reduces the patient's distress and improves the ease of insertion, by making it possible to predict the propulsion state of the distal end of the insertion section in real time using the information on the present state of the insertion section 11.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus comprising:
a flexible insertion section configured to be inserted into a subject;
an insertion section state detecting sensor configured to detect a current state of the insertion section as detection information when the insertion section is inserted into a subject; and
at least one controller configured to:
predict, using the detection information, a future propulsion state of a distal end of the insertion section and a corresponding state of the subject if the insertion section is further advanced in the subject from the current state of the insertion section; and
produce an output based on the prediction;
wherein the at least one controller predicts the propulsion state of the distal end of the insertion section and the corresponding state of the subject by one or more of:
using a calculation model of the insertion section and a calculation model of the subject, and
using the calculation model of the insertion section and the calculation model of the subject and an insertion pattern created based on past insertion data; and
the at least one controller estimates an external force applied to the insertion section from the subject, creates the calculation model of the subject based on the detection information and information on the estimated external force, and performs the prediction of the propulsion state of the distal end of the insertion section using the information on the external force and the calculation model of the subject.

2. The flexible tube insertion apparatus according to claim 1, wherein the insertion section state detecting sensor comprises one or more of a shape detecting sensor configured to detect a shape of the insertion section, a strain detecting sensor configured to detect a bend or a strain of the insertion section, a contact force detecting sensor configured to detect a contact force of the insertion section against the subject.

3. The flexible tube insertion apparatus according to claim 1, further comprising a memory that stores a value of viscoelasticity of the insertion section, wherein
the at least one controller creates an insertion section model based on information stored in the memory, and calculates an external force applied to the insertion section using the detection information and the insertion section model.

4. The flexible tube insertion apparatus according to claim 1, wherein the output comprises a warning that informs an operator of one or more of a prediction result of the propulsion state and a change of the state of the insertion section to propel the distal end of the insertion section based on the prediction result of the propulsion state.

5. The flexible tube insertion apparatus according to claim 4, wherein the warning informs the operator that the distal end of the insertion section is predicted to be in a stuck state with less propulsion force, by one or more of displaying characters, displaying an image, displaying a blinking, generating a vibration and generating a sound.

6. The flexible tube insertion apparatus according to claim 1, wherein the output comprises changing one or more of at least a contact force between the subject and the insertion section, a contact angle and a frictional force.

7. The flexible tube insertion apparatus according to claim 1, wherein the output comprises changing one or more of a bending stiffness of the insertion section, a bending angle of the insertion section, a weight distribution of the insertion section and one or more of the contact force and the contact angle of the insertion section against the subject.

8. The flexible tube insertion apparatus according to claim 7, wherein the insertion section further comprises a plurality of variable stiffness materials configured to change the bending stiffness of at least a portion of the insertion section, wherein the at least one controller is configured to change the bending stiffness of the variable stiffness material at a desired longitudinal position of the insertion section.

* * * * *